United States Patent
Guziak et al.

[11] Patent Number: 6,162,216
[45] Date of Patent: Dec. 19, 2000

[54] METHOD FOR BIOPSY AND ABLATION OF TUMOR CELLS

[76] Inventors: Robert Andrew Guziak; Judith Lynn Guziak, both of 2111 Peak Pl., Thousand Oaks, Calif. 91362

[21] Appl. No.: 09/033,107

[22] Filed: Mar. 2, 1998

[51] Int. Cl.⁷ .................................................. A61B 18/04
[52] U.S. Cl. .............................. 606/34; 606/42; 607/102; 128/898
[58] Field of Search ................... 607/96, 98, 99, 607/101, 102; 606/41, 42, 34; 600/562, 566, 567; 128/898

[56] References Cited

U.S. PATENT DOCUMENTS

| | | | |
|---|---|---|---|
| 3,913,583 | 10/1975 | Bross | 606/35 |
| 5,085,659 | 2/1992 | Rydell | 606/47 |
| 5,171,255 | 12/1992 | Rydell | 606/170 |
| 5,221,281 | 6/1993 | Klicek | 606/45 |
| 5,366,490 | 11/1994 | Edwards et al. | 607/99 |
| 5,370,644 | 12/1994 | Langberg | 606/33 |
| 5,370,675 | 12/1994 | Edwards et al. | 607/101 |
| 5,385,544 | 1/1995 | Edwards et al. | 604/22 |
| 5,409,453 | 4/1995 | Lundquist et al. | 604/22 |
| 5,417,687 | 5/1995 | Nardella et al. | 606/32 |
| 5,421,819 | 6/1995 | Edwards et al. | 604/22 |
| 5,423,809 | 6/1995 | Klicek | 606/38 |
| 5,435,805 | 7/1995 | Edwards et al. | 604/22 |
| 5,470,308 | 11/1995 | Edwards et al. | 604/22 |
| 5,470,309 | 11/1995 | Edwards et al. | 604/22 |
| 5,484,400 | 1/1996 | Edwards et al. | 604/22 |
| 5,486,161 | 1/1996 | Lax et al. | 604/22 |
| 5,507,743 | 4/1996 | Edwards et al. | 604/41 |
| 5,531,676 | 7/1996 | Edwards et al. | 604/22 |
| 5,558,671 | 9/1996 | Yates | 606/38 |
| 5,578,030 | 11/1996 | Levin | 606/39 |
| 5,607,389 | 3/1997 | Edwards et al. | 604/22 |
| 5,843,075 | 12/1998 | Taylor | 606/34 |
| 5,964,717 | 10/1999 | Gottlieb et al. | 600/567 |

*Primary Examiner*—Linda C. M. Dvorak
*Assistant Examiner*—R. Kearney
*Attorney, Agent, or Firm*—Carol D. Titus; James J. Leary; Gregory Scott Smith

[57] ABSTRACT

A medical instrument including a cannula or probe used to penetrate tissue to a target area to perform a medical procedure including biopsy and RF ablation of undesirable tissues or cells for treatment, or to prevent the spread of cancer cells during a biopsy procedure. The probe is preferably shape changeable. The probe may be hollow or solid having an exterior surface coated with a dielectric material, a preferably sharpened beveled tip at a distal end coated with a resistor material, and means for coupling the probe to an RF generator and control device. The RF generator provides current to the probe. The dielectric material provides a predominant impedance characteristic of the probe in contact with tissue, thus changes in impedance will vary primarily based on the area of the probe in contact with tissue. The control device monitors the impedance of the probe and based thereon calculates the area of the probe in contact with tissue, then adjusts the current in order to maintain an approximately constant current density over the area of the probe in contact with tissue, thereby preventing hot spots and fulguration. A thermocouple may be formed at the tip of the probe, or other temperature sensing device may be used. If a temperature sensing device is used, the control device may also monitor the temperature to determine the efficacy of treatment. RF energy directors may be used with the invention to control the shape of the RF energy field.

5 Claims, 6 Drawing Sheets

Figure 7
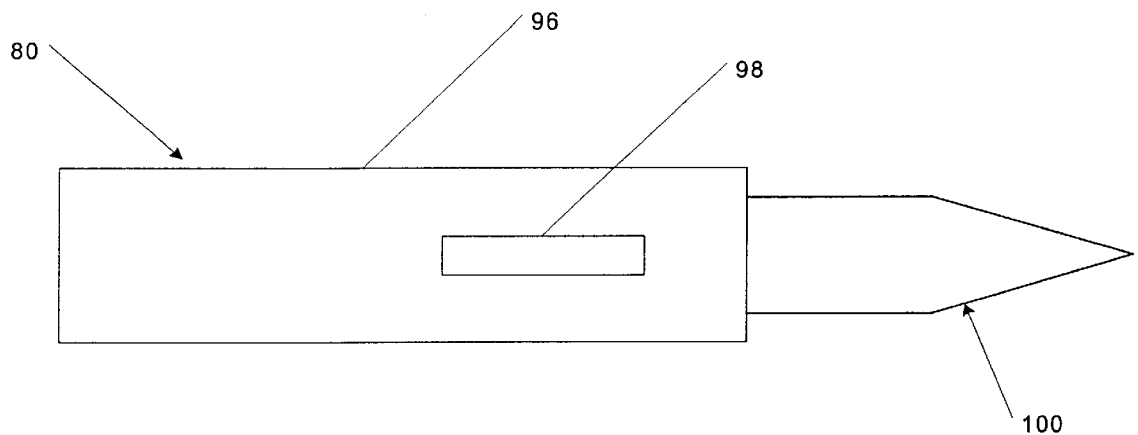
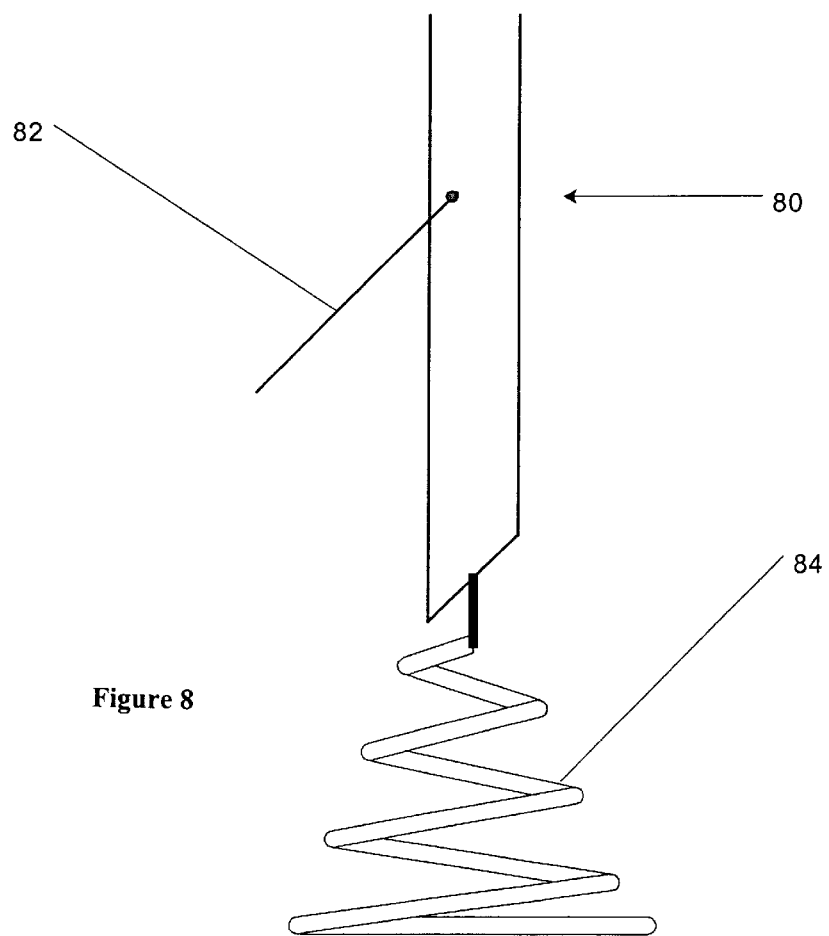
Figure 8

METHOD FOR BIOPSY AND ABLATION OF TUMOR CELLS

TECHNICAL FIELD

This invention is directed towards an apparatus and method for penetrating body tissues to precisely position a probe in a selected target area for medical purposes, for example, obtaining a biopsy tissue sample, radiofrequency energy (RF energy) treatment of tumor cells, and or delivery of substances.

BACKGROUND ART

Surgical intervention in the treatment of tumors usually involves the opening of surface tissues and excision of the underlying tumor. This excision often involves the removal of healthy tissue along with the tumor tissue to insure complete removal of the affected cells. Surgical procedures, while effective, leave scarring and wounds which are open to infectious complications, and often result in long recovery periods. Surgical intervention is often imprecise in accessing affected tissue and may damage tissue structures such as nerves, muscle, and bone to achieve access to the tumor. Consequently, minimally invasive medical procedures are of interest in many circumstances in order to reduce the trauma suffered by normal or healthy tissue.

Where devices are used to perform tissue biopsy or are manufactured for deep surgical access, such procedures generally use a tubular probe to penetrate body tissue to reach a target tissue for biopsy or treatment. These prior art devices for biopsy or cancer treatment require direct contact between a target tissue and a medical instrument. Therefore, during a biopsy or cancer treatment procedure, cancer cells may become dislodged leading to spread of the cancer cells. For example, withdrawal of the biopsy probe may leave a trail of displaced cancer cells in the wake of the withdrawn probe. During localized treatment of a tumor, cancer cells may be dislodged and moved sufficiently from the treatment area to avoid the negative effects of the treatment procedure, and dislodged cancer cells may be carried through the blood or lymph systems to lodge in locations remote from the original tumor.

Some prior art surgical instruments have been disclosed that use electrical energy to heat the instrument for cauterization purposes. For example, U.S. Pat. No. 5,578,030, issued to Levin, discloses a biopsy needle which use resistive heating of the needle to cauterize the path of the needle to prevent the spread of cancer cells. However, such devices can cause significant damage to healthy tissue when cauterizing, and in the case of the biopsy needle of U.S. Pat. No. 5,578,030, measures must be taken to protect the biopsied sample from the heat produced by the device.

Many other prior art devices use RP energy to cut or cauterize tissue, or to ablate tumor tissue. Most of these devices monitor tissue impedance to prevent the energy entering the tissue from exceeding a predetermine value. However, because the impedance of the tissue may vary over the area in contact with the probe, localized hot spots may occur causing damage to healthy tissue through fulguration, which is the explosive ignition of small amounts of combustible gases which have escaped from killed cells.

What is needed is a probe device which can be used in various embodiments to biopsy or treat a target tissue, and which uses RF energy to prevent the spread of cancer cells or infectious agents, during a biopsy or treatment procedure, without the danger of fulguration.

SUMMARY OF THE PRESENT INVENTION

Accordingly, the present invention comprises a medical probe apparatus having an electrical circuit including, a probe or cannula, an impedance sensing means, a control means, an RF energy generator, and a return electrode. The cannula may include an exterior surface with a dielectric coating. The dielectric coating is used to create a predominant impedance characteristic in the electrical circuit of the medical probe apparatus. The impedance sensing means senses the electrical impedance of the electrical circuit, and the control means monitors the impedance and adjusts an electrical current to the cannula based on the impedance at a given moment. More preferably, the control means monitors the impedance sensing means, calculates a surface area of the cannula in contact with tissue, and adjusts the current to maintain an approximately constant current density over a surface area of the cannula in contact with tissue.

The cannula can be hollow or solid, and if hollow may include more than one lumen. The distal end of the cannula may be sharpened and beveled and may further include a resistor coating to prevent the geometry of the sharpened end of the cannula from creating a region of high current density. Any practical dielectric material may be used for the dielectric coating including polyimide. In one embodiment, a hollow cannula may be coupled to a biopsy sampling and storage means for pulling a tissue sample through the lumen into a storage chamber. Ablative RF energy is caused to surround the cannula in a protective, generally cylindrical, field used to heat around the cannula to destroy any cancer cells which may be dislodged during a biopsy, and which might spread the malignancy.

In another embodiment, The cannula may include an RF energy directing means for directing the RF energy into a desired volume of tissue for treating or ablating tumors. If the cannula includes an energy directing means, the energy directing means may comprise a sheath comprised of a resistor material slidably fitting over the cannula, which sheath may further include one or more apertures that directs the RF energy in a chosen direction or directions. In an another embodiment, the energy directing means may comprise at least one RF electrode deployable from the cannula.

The medical probe apparatus may further include a temperature sensing means such as a thermocouple on the cannula. In other embodiments, the cannula may include a cannula shape changing means for causing the cannula to bend into a desired shape. For example, the shape changing, means may include a pre-bent stylet that is inserted into the lumen, if the cannula is hollow, whereby the cannula conforms to the shape of the pre-bent stylet.

The invention also includes a method for controlling the current density on the surface of the cannula in contact with tissue. The method is preferably performed by the control means and includes the following steps: (a) sensing an electrical impedance of the electrical circuit; and (b) calculating a surface area of the cannula in contact with tissue based on the impedance of the electrical circuit; and (c) adjusting the electrical current to maintain an approximately constant current density over a surface area of the cannula in contact with tissue.

More preferably, the method may include the following steps, some of which will be cyclically repeated: (a) obtaining threshold and starting values for the impedance, temperature, and the initial current, and calculating a threshold current divided by impedance value, hereafter (I/Z), (b) obtaining a new impedance value, comparing the impedance threshold to the new impedance value, reducing the current if the new impedance value exceeds the threshold impedance value; and (c) obtaining a new current value, dividing the new current value by the system impedance to obtain a present (I/Z), comparing the present (I/Z) to the threshold (I/Z), increasing the present current if the value of the present (I/Z) is less than the threshold (I/Z), decreasing the present current if the value of the present (I/Z) is more than the threshold (I/Z). The method may further include a step: (d) obtaining a present temperature value, comparing the present temperature value to the temperature set point value, and reducing the present current value if the present temperature value exceeds the temperature threshold value.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings, in which:

FIG. 7 shows a view of the distal end of a cannula embodiment for use in ablating tumor tissue with a retractable and rotatable slotted sheath RF energy director.

FIG. 8 is a view of the distal end of a cannula embodiment for use in ablating tumor tissue with two wire RF energy directors extended.

DETAILED DESCRIPTION

The present invention is an apparatus for penetrating body tissues to precisely position a cannula in a selected target area in order to perform a medical function, such as obtaining a biopsy sample or delivering ablative energy or a treating substance. The cannula includes a means for delivering RF energy to heat tissue above a critical temperature to cause the tissue to become non-viable. This invention limits activity to the precise target region, thereby minimizing trauma to normal surrounding tissue. The term "cannula" as used herein is defmed as a solid, or tubular or other hollow shape probe designed to be passed through normal tissue to target tissues. The description of the invention herein will focus on use of the invention for the biopsy or treatment of tumors, however, the device has other uses, including but not limited to the biopsy or treatment of localized infections or removal of undesirable but noncancerous tissues.

Figure 1:
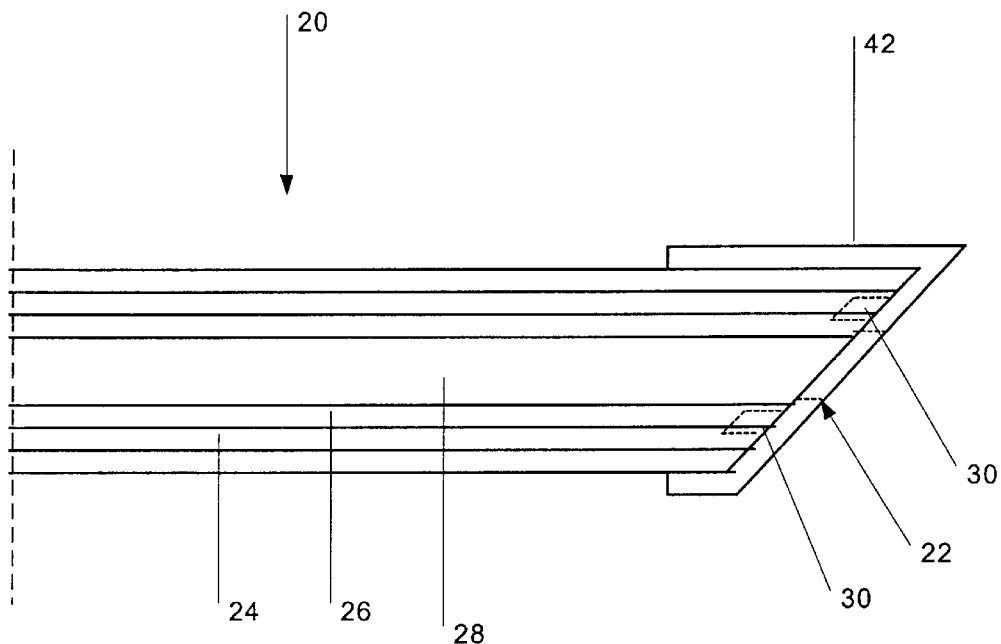
FIG. 1 is a cross-sectional view of the distal end of a cannula of the invention.

Referring to FIG. 1, a cross section of the distal end 22 of the cannula 20 of the invention is shown. The cannula 20 includes a first hollow tube 24, preferably formed of stainless steel, and a second hollow tube 26 received within the first hollow tube 24. The second hollow tube 26 is preferably formed of a metal dissimilar to the metal used in the first hollow tube 24, and at least one lumen 28 is formed inside of the second hollow tube 26. Any acceptable metal may be used for the second tube 26, however, preferred metals include copper, nickel, and nitinol. If dissimilar metals are used, the first and second hollow tubes 24, 26 are preferably welded together at the distal end 22 of the cannula to form a thermocouple. The welded region 30 joining the hollow tubes 24, 26 and formring the thermocouple can be a spot weld, but is preferably a weld over the entire circumference of the distal end 22. The distal end 22 of the cannula 20 is preferably a sharpened beveled end to reduce resistance through, and trauma to, tissue as the cannula 20 is moved into position. The cannula 20 may be any desired diameter, but is preferably from 2 to 8 French (approximately 0.7 to 2.7 mm) in diameter.

A dielectric coating 32 of a dielectric material is applied to the exterior of the first hollow tube 24 to create a dielectric barrier around the cannula 20. Any desirable dielectric material can be used including any of a number of long chain polymers such as polyimide. The dielectric coating 32 preferably also has a thermal insulating property.

In alternate embodiments, one or more transponders or transducers could be included on the exterior surface of the cannula and coupled to an ultrasound source. Suitable transducers and transponders are well known to those skilled in the art. A transducer is a crystal that emits and reads an ultrasound signal and can also read an ultrasound signal reflected back to the transducer through a medium comprising water. A transponder emits a signal only.

Figure 2:
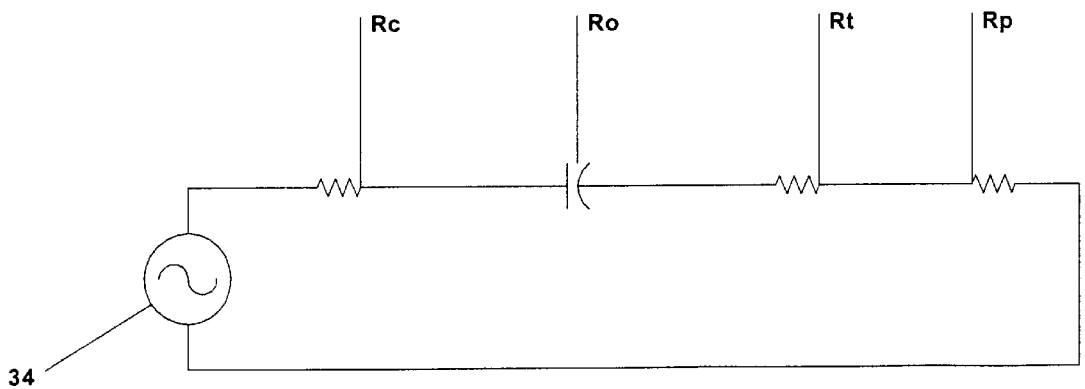
FIG. 2 is a circuit diagram of resistances encountered in the electrical circuit of the invention.

The electrical path of the system and the various resistances of the system are shown schematically in FIG. 2. The electrical resistance of the tissue is modeled as a resistor $R_f$. An RF generator 34 provides current to the cannula 20. The RF generator will generate current preferably of a sinusoidal wave form at a frequency between 200 Khz and 3 Mhz, but more preferably between 300 Khz and 2 Mhz, and most preferably at 500 Khz for use in organs, and at 750 Khz for use in other tissue.

The cannula 20, not including the dielectric coating, has a resistance (the cannula resistance $R_c$) in the range of 1 to 10 ohms depending on the material used. The resistance of the dielectric coating, hereafter the dielectric resistance $R_d$, is preferably between 100 to 500 ohms. The cannula 20 transmits the energy through the dielectric coating 32 into the tissue in contact with the cannula 20. Tissue resistance $R_t$ typically ranges between 25 to 150 ohms depending on the tissue. Current then passes through the tissue distributed along the cannula length to the return electrode. The return electrode resistance $R_r$ is preferably 1 to 10 ohms. The resistance of the tissue $R_t$ to the RF energy is used to heat tissue near the cannula 20. The target temperature range is preferably 54 degrees centigrade to 100 degrees centigrade, with 60 degrees centigrade being the most preferred target temperature. Tissue current density drops at roughly the inverse square of the distance from the cannula 20. Therefore, significant heating occurs only relatively near the cannula 20.

As is evident from the resistances set forth above, the dielectric resistance $R_d$ is relatively large compared to other resistances in the circuit. In general, the cannula resistance $R_c$ and the return electrode resistance $R_r$ are small and can be considered negligible. Thus, the dielectric resistance $R_d$ creates a predominant impedance characteristic for the cannula 20. Localized tissue resistance variations and resistance variations due to contact pressure between the cannula 20 and tissues are relatively insignificant as compared with the resistance of the dielectric coating 32.

Consequently, a near constant impedance is presented, thus providing a relatively uniform distribution of RF energy. The approximately uniformly distributed delivery of RF energy provides for a uniform current distribution across the entire surface of the cannula 20 which limits the peak current at any point on the cannula 20. Variations in current density using the invention will preferably be no greater than 1 to 10%. Limiting the peak current reduces or eliminates localized hot spots and current density variations that cause sparks and burning. The point on the distal end 22 of the cannula 20 is coated with a resistive material 42, such as any of a variety of known long chain polymers, to prevent the geometry if the tip from creating a site of increased current density, or hot spot.

In use, the electrical impedance of the cannula 20 is inversely and approximately linearly related to the surface area of the needle in contact with tissue. The greater the area of contact between the cannula 20 and tissue, the lower the system impedance. By measuring the system impedance, as opposed to the tissue impedance measured by prior art devices, the surface area of the cannula 20 in contact with tissue can be determined. A control means adjusts the current based on changes in impedance of the system in order to maintain an approximately constant current density. For increasing impedance, the current is decreased. For decreasing impedance, the current is increased. The control means may comprise a computer, which may include a display device for numerically or graphically displaying information relating to the positioning and functioning of the device of the invention.

Figure 3:
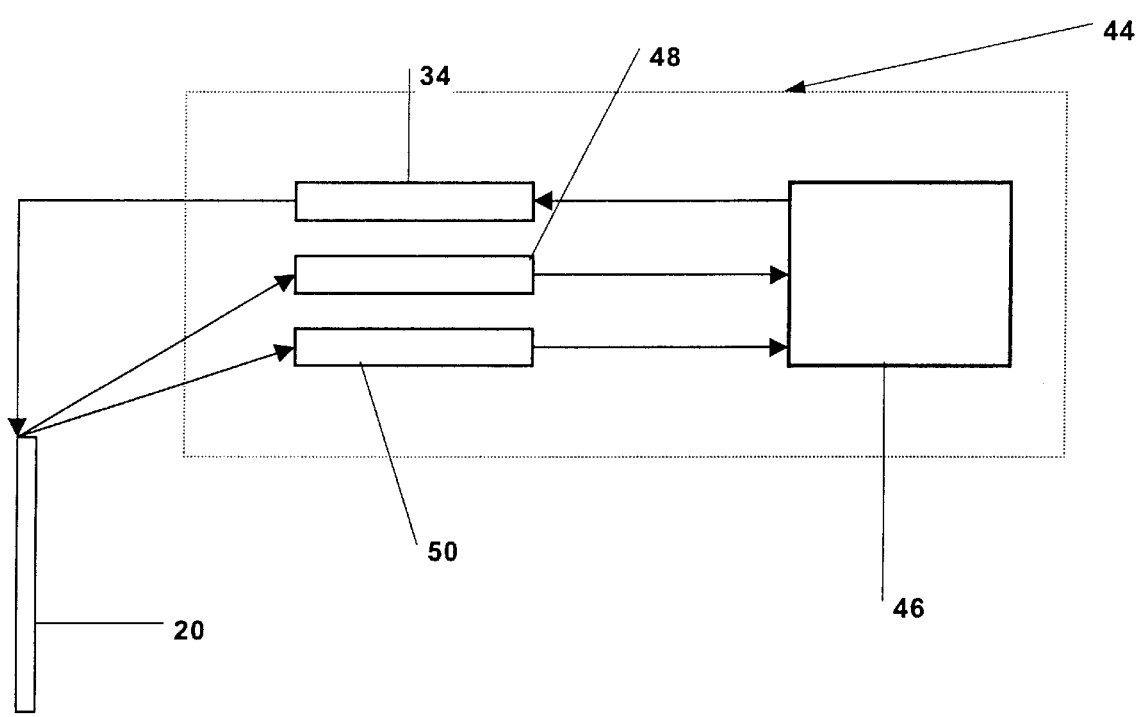
FIG. 3 illustrates a typical configuration of a control and power assembly of the invention.

A typical configuration of the control system and RF generator, generally referenced by the number 44, is shown in FIG. 3, including a control means 46 coupled to the RF current generator 34 which is coupled to the cannula 20. The cannula 20 is coupled to an impedance sensing means 48 and a temperature sensing means 50, which impedance sensing means 48 and temperature sensing means 50 are further coupled to the control means 46. The control means 46 monitors the system impedance and the temperature, if a temperature sensing means is present. The impedance is used to determine the area of the cannula 20 in contact with tissue. The current is then adjusted to maintain an approximately constant current density over the cannula 20. The temperature is monitored and used as a back-up in case the impedance sensing means is not working correctly. If the heat rises above a threshold limit, the current is reduced. Any known means for sensing temperature may be used, including the use of the thermocouple previously mentioned, or a thermistor having a resistance which varies with temperature changes, or the like.

In embodiments using a thermocouple on the distal end 22 of the cannula 20, the thermocouple can be used to sense the temperature at a position remote from the dielectric material coated portion of the cannula 20. Due to the heat insulation property of the dielectric coating and of the resistor material 42 covering the distal end 22 of the cannula 20, the thermocouple will tend to encounter heat as a result of conduction from tissue through the thermally insulating resistor material 42 rather than through the conduction of heat through the metal tubes 24, 26. Thus when the thermocouple has detected the target temperature, this indicates that the heat generated by the RF energy has penetrated tissue at least to a depth equal to the distance of the thermocouple from the dielectric coated portion of the cannula 20 in contact with tissue.

Figure 4:
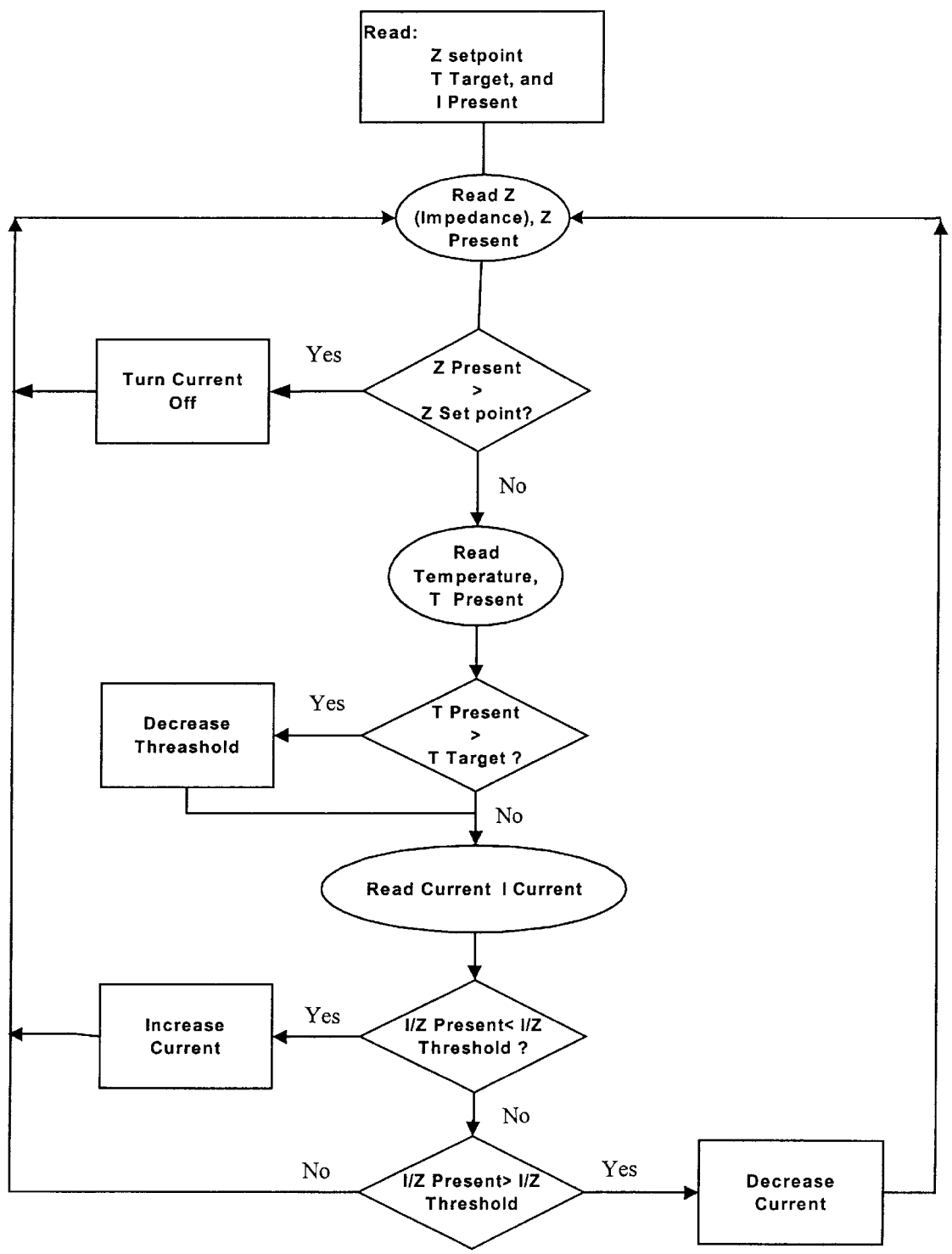
FIG. 4 is a schematic block diagram of a microprocessor controlled monitoring apparatus for controlling the RF energy delivered by the cannula of the invention.

Referring now to FIG. 4, a flow chart illustrates a method of the invention controlled by a control means that is preferably a microprocessor. When the device of the invention is turned on, the control means 46 reads the following setable predetermined thresholds or set point values: Impedance set point or threshold ($Z_{setpoint}$), temperature set point or threshold ($T_{target}$), and total current in the system ($I_{present}$). The selected initial $I_{present}$ depends on the configuration of the device, but typically ranges from 100 to 1,000 M.A. The temperature setpoint $T_{target}$ preferably ranges from 54 to 100 degrees centigrade, and most preferably is 60 degrees centigrade. Typically the threshold or set point values for $Z_{setpoint}$ and $T_{target}$ will not be changed during a procedure. However, in alternate embodiments the device may be configured to allow changes to the set point or threshold values $Z_{Setpoint}$ and $T_{target}$ during a procedure.

When the system is turned on, the system looks for a signal that an RF switch has been actuated and RF current is flowing. After the RF switch is activated, a sequence of threshold verifications is made. First the system reads a new or present impedance $Z_{present}$. The value $Z_{present}$ is compared against the impedance setpoint $Z_{setpoint}$. If the value of $Z_{present}$ exceeds the value of $Z_{setpoint}$, the current is turned off. If the impedance setpoint $Z_{setpoint}$ is not exceeded, the system reads a new or present temperature $T_{present}$. The value of $T_{present}$ is compared against the temperature set point $T_{target}$. If the value of $T_{present}$ exceeds the value of $T_{target}$ the current $I_{present}$ is reduced a predetermined amount. If $T_{target}$ is not exceeded, the system reads a new $I_{present}$ value. The control means then divides the present value for $I_{present}$ by the present value for $Z_{present}$ to generate an $(I/Z)_{present}$ value. The value $(I/Z)_{present}$ is compared to a threshold I/Z threshold value $(1Z)_{theshold}$. If the value of $(I/Z)_{present}$ is less than the threshold value $(I/Z)_{threshold}$, the current $I_{present}$ is increased and the cycle begins again. If $(I/Z)_{present}$ exceeds the threshold value, the current is decreased and the cycle begins again. If the value of $(I/Z)_{present}$ is equal to the $(I/Z)_{threshold}$, no change is made to $I_{present}$, and the cycle begins again.

The cycle can be repeated at any desirable rate, however it is preferable that the control means repeat the cycle at least 10 times per second. In operation, impedance rises to infinity when no portion of the probe is in contact with tissue. Therefore, the device cannot be activated when there is no tissue contact because, when the system determines that the impedance is greater than the set point, the system will turn the current off.

The invention described herein can be used to perform a variety of medical procedures, however, two principle configurations will be described. The first application is as a biopsy needle. In this embodiment, ablative RF energy is caused to surround the cannula in a protective, generally cylindrical, field. The RF energy is delivered into tissue providing resistive heating of the tissue approximately 10 cell layers deep around the cannula. This heating is sufficient to destroy any cancer cells which may be dislodged during a biopsy, and which might otherwise be carried through the blood or lymph systems to lodge in a remote location, thereby spreading the malignancy. The second use of the cannula is to deliver RF current therapeutically to eliminate malignant tumor tissue. The RE energy is directed as necessary into tumor tissue to eliminate the tumor tissue.

In a cannula 20 of the invention configured for use as a biopsy needle, the cannula 20 contains at least one lumen. If more than one lumen is used, the lumen for taking the biopsy sample is referred to as the first lumen. The first lumen is open at both the distal end and proximal end, which is coupled to a sample chamber. The device is preferably used as a fine needle aspiration biopsy device which is moved back and forth through the tissue that is being biopsied, and which device includes a vacuum means for pulling the sample through the lumen of the cannula 20 into a collection or sampling container. During extraction the needle is typically pulled from the tissue quickly In alternate embodiments, the cannula 20 contains a second lumen. The second lumen is preferably closed at the distal end but opened at the proximal end. In one embodiment, pre-bent stylets can be inserted into the proximal end of the second lumen, causing the cannula to bend to conform to the shape of the pre-bent stylet. Alternatively, a shape memory metal such as nitinol may be inserted in the first lumen, wherein the shaped memory stylet is inserted in a straight configuration, then heated to cause the stylet to assume a predetermined shape assumed by the memory metal after heating, as is well known in the art, causing the cannula 20 to bend to conform to the desired shape. In another embodiment, a temperature sensing device can be inserted within the second lumen to monitor the temperature inside the cannula.

Figure 5:
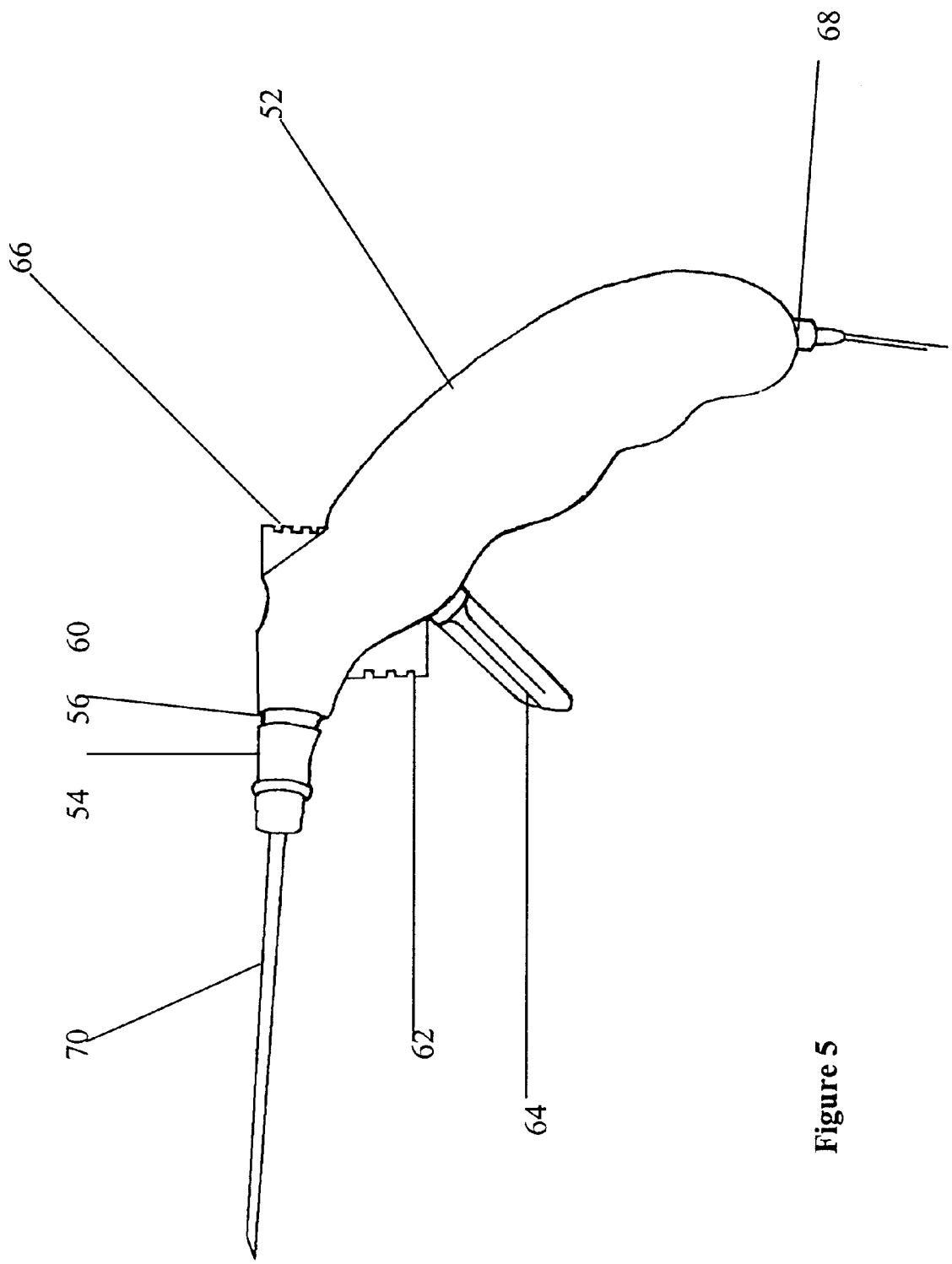
FIG. 5 is a side view of an embodiment of the invention for use in obtaining biopsy samples showing the cannula attached at its proximal end to a handle apparatus.

FIG. 5 is a side view of an embodiment of the invention for obtaining tissue samples, showing the cannula 20 of the invention coupled to a handle member 52. The device includes a cannula 20, coupled to a rotatable coupling 54 rotatably coupled to a sample chamber 56, which is coupled to the biopsy device handle member 52 at a connection hub 60. The chamber opens to the proximal end of the cannula 20. The handle member 52 includes an activation trigger 62, which is used to manually turn the current to the cannula 20 on and off. The handle member 52 further includes a sampling vacuum trigger 64 and a thumb press 66. The thumb press 66 is preferably positioned so that pressure from the thumb onto the thumb press 66 is in approximate axial alignment with the cannula 20. The user applies pressure to the thumb press 66 in order to insert the cannula 20 into tissue. The vacuum trigger 64 is coupled to a vacuum means in the handle member 52 and is actuated to create a vacuum during movement of the cannula 20 to pull sample material into the sample chamber 56. The handle member 52 has a roughly pistol grip shape for comfortable gripping by the user. Alternatively, other handle/cannula configurations may also be used. At one end of the handle member 52 a socket 68 is provided for removably coupling to the RF generator and control system 54 and power source, which preferably includes means for adjusting various parameters such as certain setable threshold or set point values.

In this embodiment the cannula 20 preferably has an exterior diameter between 0.025 inches and 0.150 inches, but most preferably of 0.050 inches, and an interior diameter between 0.010 inches and 0.050 inches, but most preferably of 0.030 inches. During biopsy, the cannula 20 is moved in and out of the target tissue with the vacuum means operating to take a sample. As previously described, the impedance circuit of the system includes the cannula 20, the tissue interface, the tissue, the return electrode, and the interconnect wires. The impedance is monitored and current is adjusted, as previously described, to maintain approximately constant current density to prevent fulguration. The current is activated during the biopsy procedure in order to cause cells that may be dislodged by the cannula 20 to become nonviable.

Figure 6:
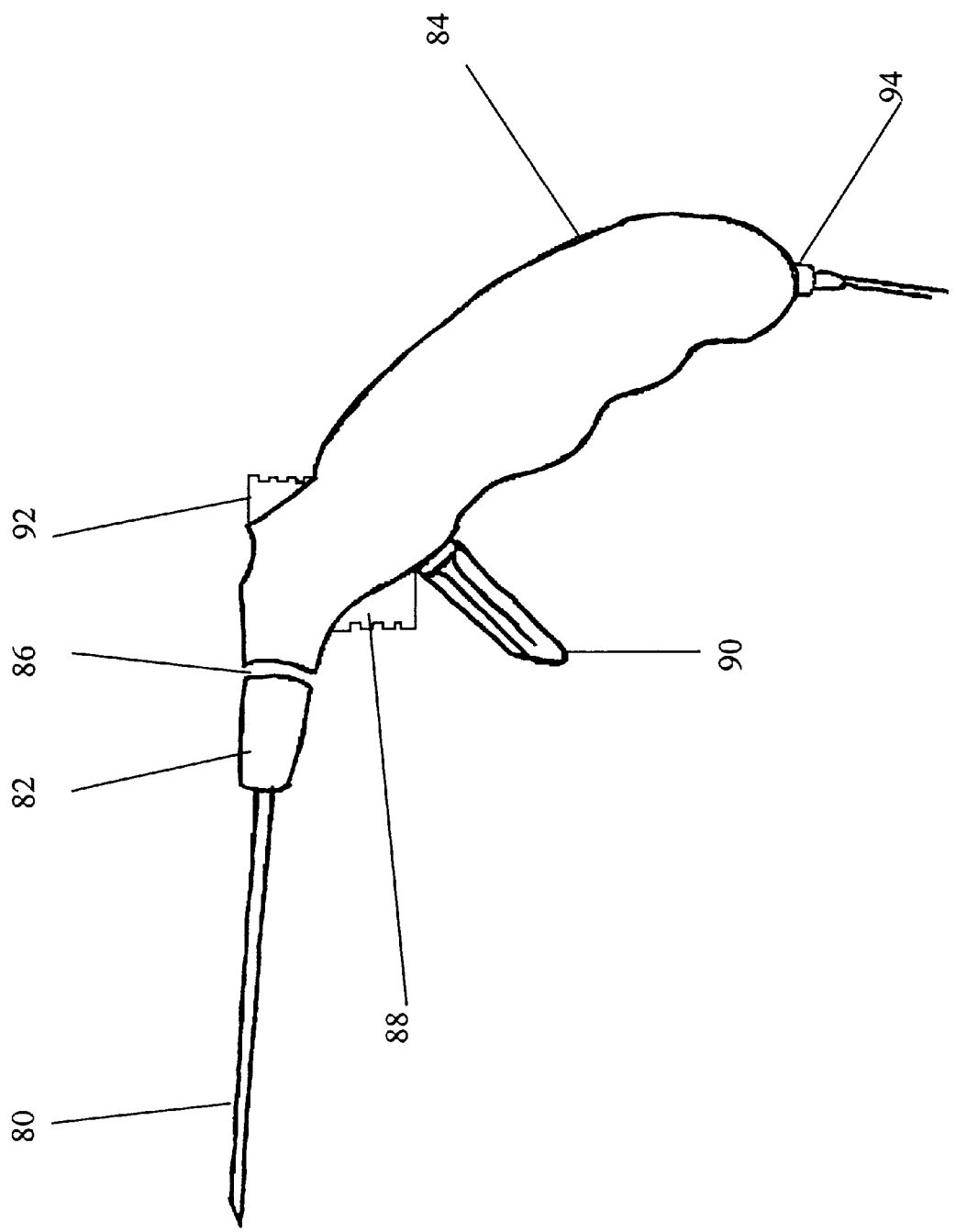
FIG. 6 is a side view of an embodiment of the invention for use in ablating tumor tissue showing the cannula atfached at its pr oximal end to a handle apparatus.

A second embodiment of the cannula is configured to deliver RF current therapeutically to eliminate malignant tumor tissue. Referring to FIG. 6, the embodiment of the device of the invention for use in ablating tumors appears similar to the biopsy device shown in FIG. 5. However, other configurations of the invention may be used. It is preferred that the device shown in FIG. 6 include a means for directing the RF energy to the target tissue while sparing healthy tissue.

The basic device shown in FIG. 6 includes a cannula 80, coupled to a rotatable coupling 82 rotatably coupled to the biopsy device handle member 52 at a connection hub 86 such as a luer connection having electrical contacts. The handle member 52 includes an activation trigger 88 which is used to manually turn the current to the cannula 80 on and off. In the embodiment shown, the handle member 52 further includes a trigger 90 for manipulating an energy directing means to control the shape of the RF energy field generated. A thumb press 92 is preferably positioned on the handle member 52 so that pressure from the thumb onto the thumb press 92 is in approximate axial alignment with the cannula 80. The user applies pressure to the thumb press 92 in order to insert the cannula 80 into tissue. Preferably, the handle member 52 has a roughly pistol grip shape for comfortable gripping by the user, and a socket 94 is provided for removably coupling to the control assembly and power source 44. The cannula 80 may be solid in this embodiment, or may be hollow having one or more lumens. If the cannula 80 is hollow, the lumen may be used as previously described for insertion of pre-bent stylets or the like to cause the cannula 80 to conform to a desired shape prior to use. The cannula 80 preferably has an exterior diameter between 0.025 and 0.15 inches, but most preferably 0.050 inches, and if the cannula 80 is hollow, an interior diameter between 0.010 inches and 0.050, but most preferably 0.030 inches The cylindrical exterior of the cannula delivers only an approximately cylindrical energy pattern, however, a variety of means for directing the energy into a variety of configurations to ablate tumors of many shapes and sizes may be used.

Referring to FIG. 7, a hollow insulating sheath 96 may be made to fit over the cannula 80. After insertion into the tumor, the insulating sheath 96 may be retracted. This allows the size of the energy cylinder to be varied, thereby varying the therapy delivery area. In an alternate embodiment, the insulating sheath 96 may have a slot or other shape aperture thereon. For example, FIG. 7 shows an embodiment of the cannula 80 of the invention with a slot 98 positioned longitudinally on the external sheath 96, providing a means of directing energy in one direction. By rotating and advancing or retracting the sheath 96, the slot 98 can be directed as needed to progressively ablate a complex geometry. In this embodiment, a resistive coating is applied to the distal end 100 of the cannula 80 for a distance along the length of the cannula 80 sufficient to allow the retraction of the sheath 96 a desired distance without exposing the dielectric coating.

Referring to FIG. 8, a cannula having at least one lumen can be used to advance energy directing conductors into target tissue. FIG. 8 shows a first conductor 82 which is straight and is advanced or deployed through an aperture in the side of the cannula 80, and a second antenna 84 that is extended or deployed through the distal end of the cannula 80, and is in a pre-bent spiral configuration. However, any desirable configuration or number or shape of antenna could be used, depending on the geometry of the area to be treated. The antennae are preferably formed of, or coated with, a biocompatible dielectric material. The conductors 82, 84 may include transponders or transducers to aid in positioning the antennae precisely.

Although the present invention has been described in terms of the presently preferred embodiments, it is to be understood that such disclosure is not to be interpreted as limiting. Various alterations and modifications will no doubt become apparent to those skilled in the art after reading the above disclosure. For example, the invention could be used to treat localized infections instead of tumors by using the RF energy to cause the infectious agents to become non-viable. Accordingly, it is intended that the appended claims be interpreted as covering all alterations and modifications as fall within the true spirit and scope of the invention.

What is claimed is:

1. In a medical probe apparatus comprising a cannula with an exterior surface with a dielectric coating, the dielectric coating having a predominant impedance characteristic in an electrical circuit of the medical probe apparatus, an impedance sensor, a control means for adjusting an electrical current to the cannula, an RF energy generator, and a return electrode, a method for controlling or maintaining an approximately uniform current density over a surface area of the cannula in contact with tissue, the method steps comprising:

(a) obtaining the following values:
      (i) obtaining an impedance threshold value,
      (ii) obtaining a starting current value, and
      (iii) obtaining a threshold current divided by impedance value, hereafter (I/Z); and
   (b) obtaining a new impedance value, comparing the impedance threshold to the new impedance value, reducing the current if the new impedance value exceeds the threshold impedance value; and
   (c) obtaining a new current value, dividing the new current value by the system impedance to obtain a present (I/Z), comparing the present (I/Z) to the threshold (I/Z), increasing the present current if the value of the present (I/Z) is less than the threshold (I/Z), decreasing the present current if the value of the present (I/Z) is more than the threshold (I/Z).

2. The method of claim 1, wherein step (a) further comprises the sub-step:

(iv) obtaining a temperature threshold value.

3. The method of claim 2, further comprising the step:

(d) obtaining a present temperature value, comparing the present temperature value to the temperature set point value, reducing the present current value if the present temperature value exceeds the temperature threshold value.

4. The method of claim 1 further comprising the step:

(e) repeating steps (b) and (c).

5. The method of claim 1 further comprising the step:

(e) repeating steps (a) through (c).

* * * * *